United States Patent [19]

Wilson

[11] 3,966,160

[45] June 29, 1976

[54] INFLIGHT INTRAVENOUS BOTTLE HOLDER

[75] Inventor: Myrl E. Wilson, Sheppard AFB, Tex.

[73] Assignee: The United States of America as represented by the Secretary of the Air Force, Washington, D.C.

[22] Filed: May 12, 1975

[21] Appl. No.: 576,504

[52] U.S. Cl............................ 248/311.3; 248/295
[51] Int. Cl.²............................................ A47K 1/08
[58] Field of Search .......... 248/318, 360, 310, 311, 248/312, 102, 103, 104, 105, 106, 132, 244, 295, 327, 328, 304, 305, 317 R; 211/74; 24/249 AP; 215/100 R, DIG. 3

[56] References Cited
UNITED STATES PATENTS

| 1,283,160 | 10/1918 | Gross | 248/311 |
|---|---|---|---|
| 1,742,619 | 1/1930 | Smith | 248/311 |
| 2,098,996 | 11/1937 | Blake et al. | 248/311 |
| 2,216,886 | 10/1940 | Langelier | 248/295 |
| 2,541,390 | 2/1951 | Weigand | 248/311 |
| 3,400,870 | 9/1968 | Divietri | 24/71.3 |

FOREIGN PATENTS OR APPLICATIONS

| 60,882 | 3/1943 | Denmark | 248/311 |
|---|---|---|---|
| 1,030,377 | 6/1953 | France | 215/DIG. 3 |

*Primary Examiner*—Roy D. Frazier
*Assistant Examiner*—Robert A. Hafer
*Attorney, Agent, or Firm*—Joseph E. Rusz; Arsen Tashjian

[57] ABSTRACT

A bottle holder assembly in a preferred embodiment adapted for use as an inflight intravenous bottle holder aboard an aircraft on an aeromedical airlift mission. The holder comprises: a cradle, generally configurated in the form of an inverted T, with an upper and a lower end and with a slot in each end, and with each end bent backwardly; a hook removably connected to the upper end; and, a strap subassembly attached to the cradle and suitably configurated and dimensioned to accept a standard intravenous bottle which is in the inverted, operative position. The intravenous bottle holder is removably attachable to, and slideably movable along, any one of the plurality of conventional litter support straps which such an aircraft is equipped. The cradle of the bottle holder is held in a gripping action with the support strap because of friction. The bottle holder is exceptionally well suited for the purpose intended, and obviates the current, unsatisfactory, use of makeshift methods to support and use the inverted intravenous bottle.

3 Claims, 5 Drawing Figures

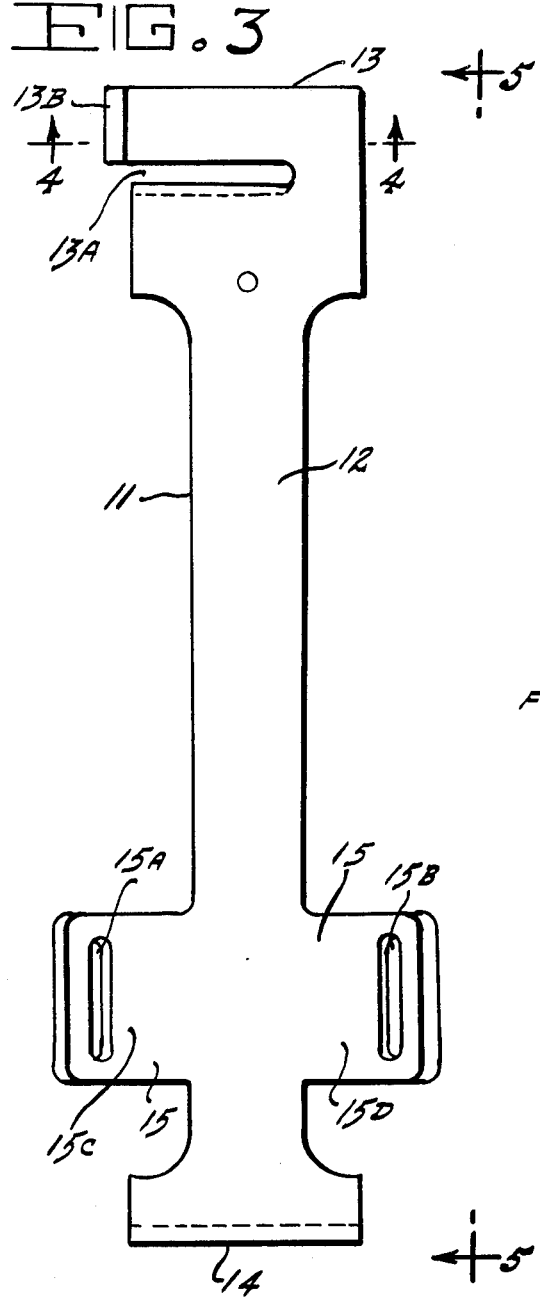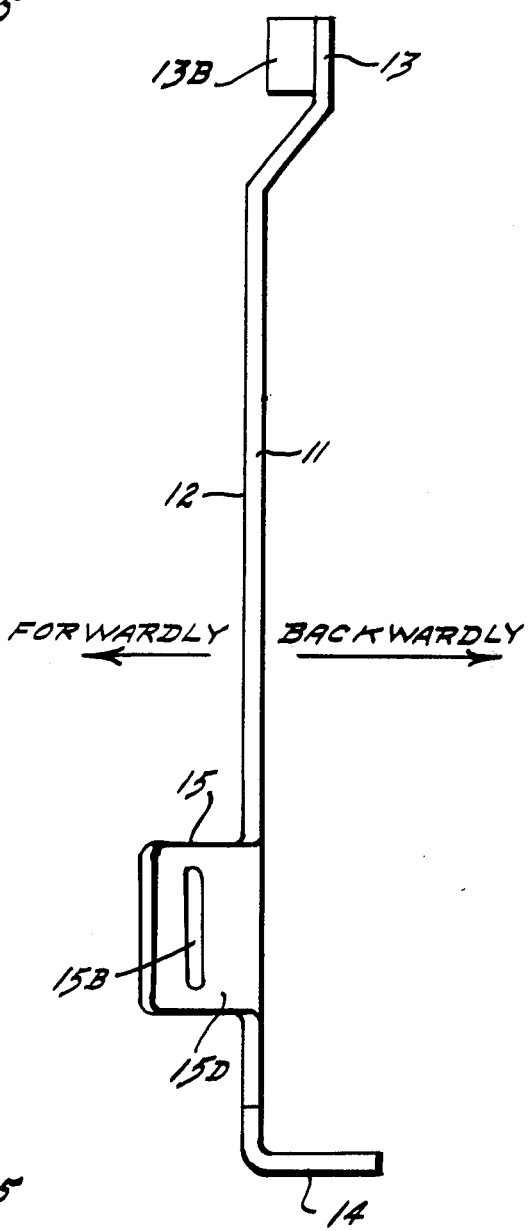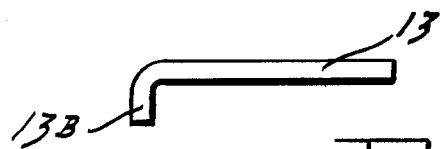

INFLIGHT INTRAVENOUS BOTTLE HOLDER

STATEMENT OF GOVERNMENT INTEREST

The invention described herein may be manufactured and used by or for the Government for governmental purposes without the payment of any royalty thereon.

BACKGROUND OF THE INVENTION

This invention relates to a container holder assembly and, more particularly, to a bottle holder assembly, adapted for use as an inflight holder of an intravenous bottle.

Presently there is no simple, satisfactory method of (or an apparatus for) suspending intravenous bottles or other hanging equipment at patients' litters while caring for litter patients during aeromedical airlift missions. The current method, which is far from being completely satisfactory, is to secure these articles with adhesive tape and gauze bandages, which at best is makeshift.

Obviously, therefore, there is a dire need for a holder, especially of an intravenous bottle, in caring for patients at their litters in the aircraft. I have invented such a holder; and, by fulfilling this need, I have significantly advanced the state-of-the-art.

SUMMARY OF THE INVENTION

An object of this invention is to provide a container holder assembly that can be used at a patient's litter in an aircraft.

Another object of this invention is to provide such a container holder assembly which is relatively inexpensive to manufacture and also is quickly attachable, easily adjustable, compact, and lightweight.

Still another object of this invention is to teach a specific preferred embodiment of the hereinabove described container holder assembly, wherein the preferred embodiment is especially adapted for use as an inflight holder of an intravenous bottle.

These objects, and other equally important and related objects, of this invention will become readily apparent after a consideration of the description of the invention, coupled with reference to the Figures of the drawings.

DESCRIPTION OF THE DRAWINGS

FIGS. 3, 4 and 5 are various views of the same major component of the preferred embodiment of the invention.

DESCRIPTION OF THE PREFERRED EMBODIMENT

Figure 1:
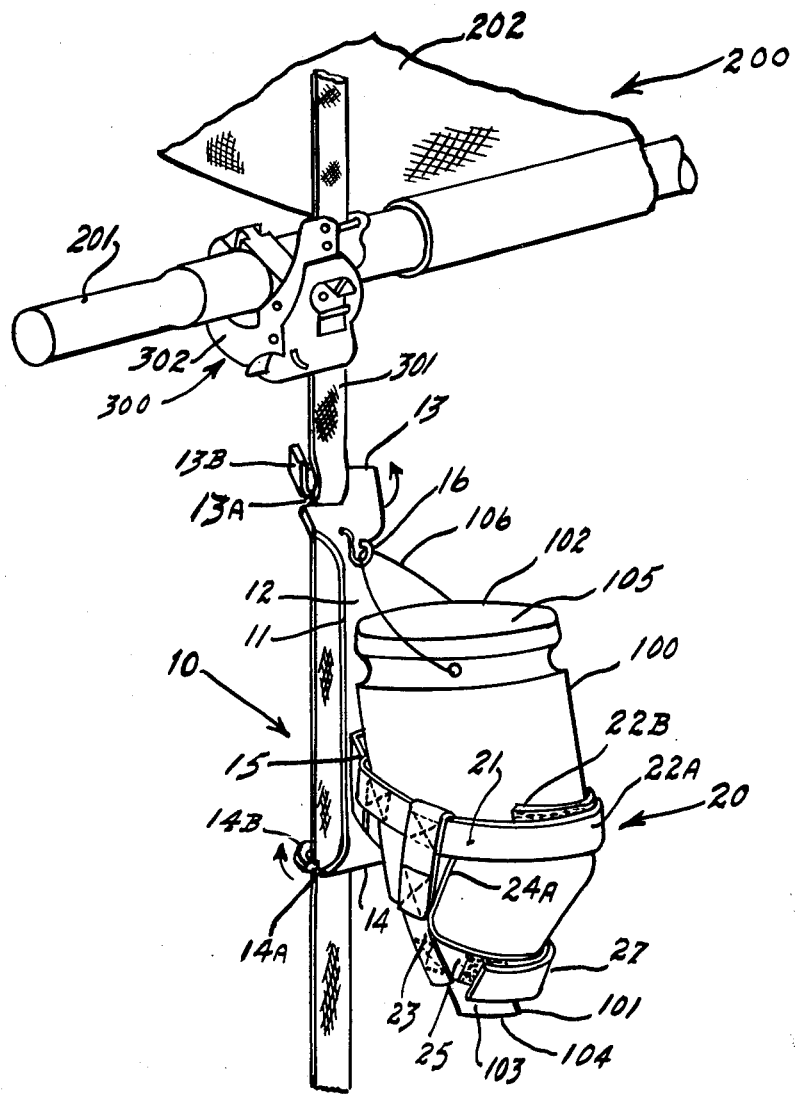
FIG. 1 is a pictorial view, in perspective, of the preferred embodiment of the invention in use in its working environment.

With reference to FIG. 1, therein is shown a preferred embodiment 10 of my inventive container holder assembly, as adapted for use in an inflight holder of an intravenous bottle 100, in its working environment in a multimission aircraft, during an aeromedical airlift operation, wherein said aircraft has a plurality of litters (i.e., medical stretchers), such as representative one 200 shown in partially fractured form, each of which said litters has (but is not limited to) a side carrying pole 201 and a canvas, or the like, bed member 202. The litters are disposed in spaced-apart horizontal position and relationship, and are also "stacked" one above the other in vertical spaced-apart position and relationship.

The aircraft also has therein a plurality of litter supports, such as representative one 300, each of which includes (but is not limited to): a vertically disposed support strap 301, conventionally made of webbed material, secured at its upper end to the interior of the aircraft; and, a carrying pole holder 302, conventionally a clasp or clamp, which also holds the vertically disposed support strap 301.

It is to be assumed, for explanatory purposes, that there is a patient in a litter vertically below representative litter 200, which said patient is to be fed, or otherwise medicated, intravenously using preferred embodiment 10 as the inflight holder of a conventional intravenous bottle, such as 100, which has two ends 101 and 102, with a neck 103 and an outlet 104 at one end 101, and a bottom 105 and a bale (i.e., a bail wire) 106 at the other end 102. It is to be noted that the intravenous bottle 100 is inverted when in use.

Still with reference to FIG. 1, the preferred embodiment 10 includes: a cradle (or bracket) 11 generally configurated in the form of an inverted T, wherein the T has a vertical leg 12 with an upper end 13 and a lower end 14, and a horizontal leg 15, and wherein the cradle 11 is suitably configurated and dimensioned so as to be removably attachable to, and slideably movable vertically along, any one of the litter support straps, such as representative one 301; a hook 16 that is removably connected to the upper end 13 of the vertical leg 12 of the inverted T-shaped cradle, with the hook 16 suitably configurated and dimensioned to accept and to hold the bale (i.e., the bale wire) 106 of the intravenous bottle 100 when the bottle 100 is in the inverted operative position; and, a strap (or harness) subassembly, generally designated 20, that is suitably configurated and dimensioned to accept, and to assist in holding and in supporting, the inverted intravenous bottle 100 at the neck 103 and outlet 104 end 101.

Again with reference to FIG. 1, the cradle 11 has a first slot 13A in the upper end 13 of the vertical leg 12 thereof, and has a second slot 14A in the lower end 14 of the vertical leg 12 thereof. Additionally, each slotted end 13A and 14A is bent backwardly, as indicated by the respective arrows, to engage with, and to frictionally hold, the litter support strap 301. Further, the upper slotted end 13 preferably has, but need not have, an upwardly extending flange 13B which assists in preventing accidental lateral slippage of the support strap 301 out of upper slot 13A. Also, the lower slotted end 14 preferably has, but need not have, a forwardly extending flange 14B also which assists in preventing accidental lateral slippage of support strap 301 out of lower slot 14A.

Both the cradle 11 and the hook 16 are preferably made of metal, with the cradle 11 preferably made of aluminum as a first preference and of stainless steel as a second preference, and with the hook 16 preferably made of stainless steel.

The strap or harness subassembly includes, but is not necessarily limited to: an upper strap 21 having a first end portion 22A and a second end portion 22B, with these portions releasably connectable to each other by suitable means; an intermediate strap 23 also having a first end portion 24A and a second end portion, with these end portions attached to the upper strap 21 at, respectively, different locations thereof 21; and, a first lower strap 25 and a second lower strap 26, wherein each lower strap 25 and 26 has two end portions, with one end portion of each lower strap attached to the intermediate strap 24 at different locations, and with each of the respective other end portions releasably connectable to each other by suitable means.

Figure 2:
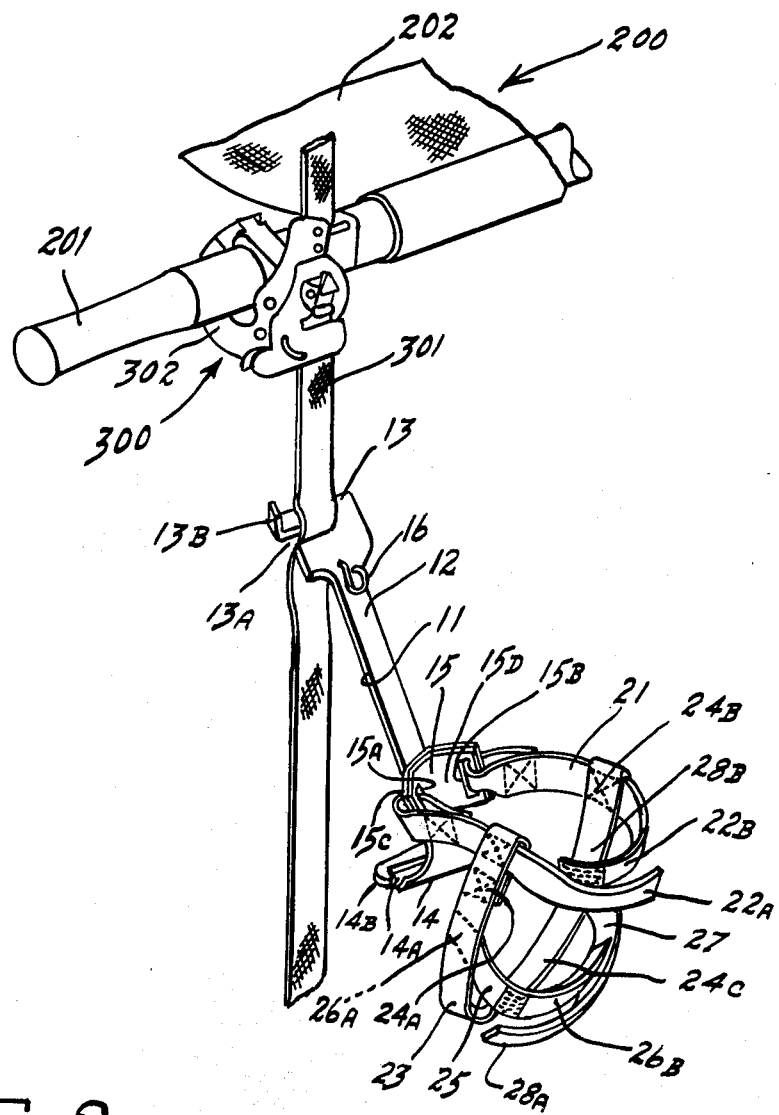
FIG. 2 is a pictorial view, in perspective, of the preferred embodiment of the invention in its working environment, although not in use.

With reference to FIG. 2, therein is shown the preferred embodiment 10 of my inventive bottle holder assembly in its working environment, as explained hereinbefore, but not in use, and not holding and supporting the intravenous bottle 100, FIG. 1.

In this view the preferred structural details of the horizontal leg 15 of the cradle 11, and of the strap subassembly 20, can be easily seen. As to the horizontal leg 15, there is a plurality of openings (in this case two of them) therein, such as representative ones 15A and 15B, to accept and to hold the strap subassembly 20 generally, and the upper strap 21 specifically. Additionally, the horizontal leg 15 has a first end area 15C and a second end area 15D which preferably are, but need not be, bent forwardly (as indicated by directional arrows) to conform to the external surface of the intravenous bottle 100, FIG. 1. As to the strap (or harness) subassembly 20, easily seen is upper strap 21 with first end portion 22A and second end portion 22B; intermediate strap 23 with first end portion 24A and second end portion 24B; and, a first lower strap 25 with first end portion 26A and second end portion 26B, and a second lower strap 27 with first end portion 28A and second end portion 28B.

It is to be noted intermediate strap 23, because of the attachment of end portions 24A and 24B to upper strap 21 at different locations thereof 21, becomes (i.e., forms in the shape of) a half loop which is generally designated 24C for identification purposes.

It is also to be remembered: that the end portions 22A and 22B of upper strap 21 are releasably connectable to each other by suitable means; and, that second end portion 26B of lower strap 25, and first end portion 28A of second lower strap 27, are also releasably connectable to each other also by suitable means. In that regard, it is to be noted that said suitable means may comprise, solely as a matter of preference, complementary "Velcro" pieces. Of course, other suitable means may be used.

It is further to be noted that each of the straps 21, 23, 25 and 27 preferable, but not necessarily, are made of nylon web material.

Now, with reference to FIG. 3, therein is shown a front view of the cradle (or bracket) component 11 of the preferred embodiment 10 of my inventive bottle holder assembly, previously shown in FIGS. 1 and 2. Also clearly shown in FIG. 3 are: vertical leg 12; horizontal leg 15; vertical leg upper end 13 with slot 13A and flange 13B; vertical lower end 14; horizontal leg first end area 15C with opening 15A; and, horizontal leg second end area 15D with opening 15B.

FIG. 4 is the view taken from, and seen along, line 4-4 in FIG. 3. Seen therein is vertical leg upper end 13 and flange 13B thereof.

Now, with reference to FIG. 5 which is the view seen from, and taken along, line 5-5 in FIG. 3, shown therein is cradle component 11. Also shown are: vertical leg 12; horizontal leg 15; vertical leg upper end 13 with flange 13B; vertical leg lower end 14; and, horizontal leg second end area 15D with second opening 15B therein. For orientation purposes, directional arrows and appropriate legends are also shown.

MANNER OF OPERATION AND/OR USE OF THE PREFERRED EMBODIMENT

The manner of operation and/or use of the preferred embodiment 10 of my inventive bottle holder assembly, as adapted for use as an inflight holder of an intravenous bottle aboard an aircraft, can very easily be ascertained by a person of ordinary skill in the art, from the foregoing description, coupled with reference to the Figures of the drawings.

For others, it is sufficient to say in explanation (and, with reference to FIGS. 1-5, inclusive) that to attach the bottle holder assembly 10 to support strap 301, firstly, the support strap 301, at the desired height, is slipped into slot 13A, and behind flange 13B, of upper end 13 of vertical leg 12 of cradle 11. Then, while the assembly 10 as a whole is pressed toward and against the support strap 301, the support strap 31 is slipped into slot 14A, and behind flange 14B, of lower end 14 of vertical leg 12 of cradle 11. In this regard, it is to be noted that, because the upper end 13 is bent backwardly, there is a substantial, frictional gripping action between the support strap 301 and the slot 13A in the bent upper end 13 of the vertical 12 of cradle 11. Likewise, there is a frictional gripping action between the support strap 301 and the slot 14A in the bent lower end 14. As a result, the assembly 10 as a whole is frictionally held suspended, and secured from the support strap 301. Nevertheless, the cradle is easily removable, if so desired, merely by reversing the abovementioned attachment procedure (i.e., unhooking the ends 13 and 14 of the vertical leg 12 of the cradle 11 from the support strap 301). On the other hand, if desired, the vertical leg 12 may be slideably moved upwardly or downwardly along support strap 301, without removing the cradle 11 from the support strap 301.

To attach the intravenous bottle 100 to the holder 10, firstly the intravenous bottle is inverted. Then, the bottle bale 106 is slipped over the hook 16. After that, the bottle 100 is encircled with the upper strap 21, by pressing the "Velcro" tape ends 22A and 22B firmly together. Then, the bottle 100 is so positioned that the back of the neck 13 at lower end 101 of bottle 100 is on, is abutting with, and is supported by the dangling half-loop intermediate strap 23. After that, the "Velcro" tape ends 26B and 28A of, respectively, lower straps 25 and 27 are overlapped and pressed firmly, thereby completing the removable attachment of the intravenous bottle 100 to the bottle holder assembly 10. To release the bottle 100 from the holder 10, the above procedure is simply reversed.

CONCLUSION

It is abundantly clear from all of the foregoing, and from the Figures of the drawings herein, that the stated and desired objects of my invention have been attained. In addition, related desirable objects also have been achieved.

It is to be noted that, although there have been described the fundamental and unique features of my invention as applied to a particular preferred embodiment, various other embodiments, adaptations, substitutions, additions, omissions, and the like will occur to, and can be made by, those of ordinary skill in the art, without departing from the spirit of my invention. For example, my invention may be adapted to hold and/or to suspend gastric and urinary drainage bags and oxygen and/or suction tubing.

What is claimed is:

1. A bottle holder assembly, adapted for use as an inflight holder of an intravenous bottle aboard an aircraft, wherein said aircraft is equipped with conventional litters and litter support straps, and wherein said intravenous bottle is of the conventional type having two ends, with a neck and an outlet at one end, and with a bottom and a bail at the other end, comprising:

a. a cradle generally configured in the form of an inverted T, wherein said T has a vertical leg with an upper end and a lower end, and a horizontal leg, and wherein said cradle is suitably configured and dimensioned so as to be removably attachable to, and slideably movable along, any one of said litter support straps;

b. a hook releasably connected to said upper end of said vertical leg of said inverted T-shaped cradle, wherein said hook is suitably configured and dimensioned to accept and to hold said bale of said intravenous bottle when said bottle is in an inverted position;

c. and, a strap subassembly removably attached to said cradle and suitably configured and dimensioned to accept, and to assist in holding and in supporting, said intravenous bottle at said neck and outlet end when said bottle is in an inverted position, wherein said strap subassembly includes:

1. an upper strap having a first end portion and a second end portion, wherein said end portions are releasably connectable;
2. an intermediate strap having a first end portion and a second end portion, with said first and second end portions attached to said upper strap at different locations respectively, thereby causing said intermediate strap to become formed in the shape of a half-loop;
3. and, a first lower strap and a second lower strap, with each said lower strap having a first and a second end portion, and with said first end portion of said first lower strap attached to said intermediate strap, and with said second end portion of said second lower strap also attached to said intermediate strap at a different location, and also with said second end portion of said first lower strap, and said first end portion of said second lower strap releasably connectable.

2. A strap subassembly, as set forth in claim 1, wherein each said strap is made of nylon web material.

3. A strap subassembly, as set forth in claim 2, wherein:

a. said first end portion and said second end portion of said nylon web upper strap each have, respectively, complementary "Velcro" pieces which render said first and second end portions releasably connectable;

b. said second end of said nylon web first lower strap and said first end portion of said nylon web second lower strap each have, respectively, complementary "Velcro" pieces which render said first and second ends releasably connectable.

* * * * *